United States Patent [19]

Klass

[11] 4,161,610

[45] Jul. 17, 1979

[54] PROCESS FOR PREPARING VINYL ESTERS

[75] Inventor: Donald L. Klass, Barrington, Ill.

[73] Assignee: Union Oil Company of California, Brea, Calif.

[21] Appl. No.: 141,832

[22] Filed: Sep. 29, 1961

[51] Int. Cl.$^2$ ............................................. C07C 67/05
[52] U.S. Cl. ................................... 560/243; 568/689; 560/64; 560/81; 560/95; 560/105; 560/113
[58] Field of Search ............... 260/614, 497, 475, 476, 260/485, 497, 410.9 UA; 560/243, 64, 81, 95, 105, 113

[56] References Cited

U.S. PATENT DOCUMENTS 3,300,528  1/1967  Wakasa .............................. 260/497 A Primary Examiner—James O. Thomas, Jr.
Assistant Examiner—Michael Shipper
Attorney, Agent, or Firm—Richard C. Hartman; Michael H. Laird

[57] ABSTRACT

This invention involves a method of producing vinyl esters by the reaction of olefins with carboxylic acids in the presence of alkali and alkaline earth metal salts of carboxylic acids, a noble metal compound, and a regenerative oxidant capable of maintaining the noble metal in oxidized form.

8 Claims, 1 Drawing Figure

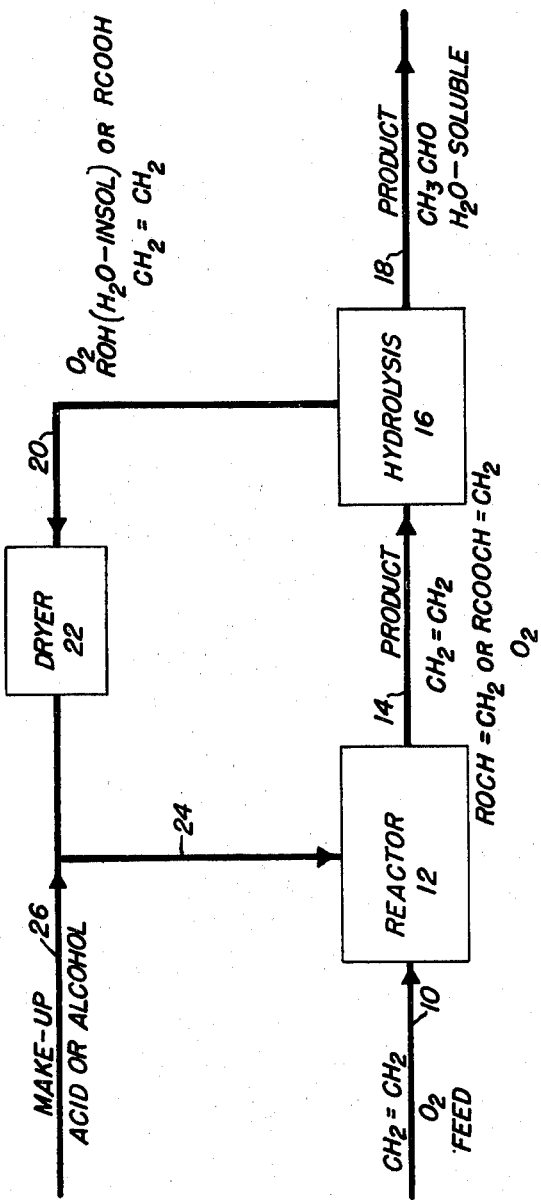

PROCESS FOR PREPARING VINYL ESTERS

This invention relates to a process for the synthesis of vinyl ethers and vinyl esters. More particularly, this invention relates to a process for the synthesis of vinyl ethers and vinyl esters from olefins and alcohols or carboxylic acids.

In accordance with this invention, vinyl esters are prepared by contacting a mixture of an olefin and a carboxylic acid with a catalyst system consisting of a compound of a noble metal from Group VIII of the Periodic Table and a regenerative oxidant capable of keeping the noble metal in oxidized form. Vinyl ethers are prepared by contacting a mixture of an olefin and an alcohol with the same type of catalyst system. The oxidant may be continuously regenerated in place by introducing an oxygen-containing gas into the reaction zone, or it may be regenerated by periodically or continuously withdrawing the catalyst system from the reaction zone, contacting it with oxygen-containing gas, and returning it to the reaction zone.

It becomes therefore a primary object of this invention to provide a process for preparing vinyl esters and vinyl ethers.

An object of this invention is to provide a process for the synthesis of vinyl ethers by reaction of olefins and alcohols.

An object of this invention is to provide a process for the synthesis of vinyl esters by reaction of olefins and acids.

An object of this invention is the provision of a process for producing vinyl ethers by the reaction of olefins and alcohols in the presence of a catalyst system consisting of a compound of a noble metal from Group VIII of the Periodic Table and a regenerative oxidant capable of keeping the noble metal in oxidized form.

Another object of this invention is to provide a process for the production of vinyl esters by the reaction of olefins and acids in the presence of a catalyst system consisting of a compound of a noble metal from Group VIII of the Periodic Table and a regenerative oxidant capable of keeping the noble metal in oxidized form.

The drawing is a flow diagram of one embodiment of this invention.

The process of this invention is conducted by maintaining the catalyst system in solution or suspension in the alcohol or acid and passing the olefin, in vapor form, through the liquid suspension. An alternative mode for carrying out the invention comprises supporting the catalyst system on an inert, particulate solid and passing a vaporized mixture of olefin and acid or alcohol through the bed of solid.

The olefinic reactants used in accordance with this invention may be any olefinic or diolefinic hydrocarbon, preferably having up to 10 carbon atoms per molecule. Suitable olefinic hydrocarbons are ethylene, propylene, alpha-butylene, beta-butylene, pentene and its homologs, cyclohexene, and styrene. Mixtures of olefins, or gases containing olefins or other unsaturated compounds, may be used in the reaction of this invention provided they are capable of reacting under the reaction conditions. The reaction of olefins containing two to three carbon atoms constitutes a preferred group of starting materials. Under certain reaction conditions, it may be necessary to adjust the temperature and pressure so that the reaction will go forward with particular olefins, taking into account their physical properties. Where higher olefins are used, the products will have correspondingly higher boiling points which may also require corresponding modifications in the reaction conditions.

The alcohols used in accordance with this invention may comprise any primary, secondary, or tertiary alcohol containing 1 to 20 carbon atoms. Examples of alcohols coming within this formula are methyl, ethyl, propyl, isopropyl, butyl, isobutyl, t-butyl, amyl, isoamyl, neopentyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, and eicosyl alcohol. Other alcohols that can be used include pentanol-2, methylisopropyl carbinol, t-amyl alcohol, 2-methylpentanol-1, 3-methylpentanol-1, t-amyl carbinol, 2-ethylbutanol-1, neopentyl carbinol, 2,3-dimethylbutanol-1, hexanol-2, hexanol-3, 3-methylpentanol-2, methylisobutyl carbinol, ethylisopropyl carbinol, pinacolyl alcohol, 2-methylpentanol-2, methyldiethyl carbinol, dimethylisopropyl carbinol, diisopropyl carbinol, 2,4-dimethylpentanol-1, pentamethylethanol, capryl alcohol, lauryl alcohol, pentadecanol-1, cetyl alcohol, carnaubyl alcohol, aryl alcohol, montanyl alcohol, ginnol, melissyl alcohol, myricyl alcohol, gossypyl alcohol, lacceryl alcohol, and psyllicyl alcohol.

The acids used in accordance with this invention have the formula $R'(COOH)_m$, wherein $R'$ is any hydrocarbon radical having 1 to 20 carbon atoms and m has the value of 1 to 5.

Where $R'$ is an aliphatic radical, the following acids are intended:
  acetic acid
  propionic acid
  n-butyric acid
  isobutyric acid
  n-valeric acid
  trimethyl acetic acid
  caproic acid
  n-heptylic acid
  caprylic acid
  pelargonic acid Where $R'$ is an aromatic radical, an alkylaryl radical, an aralkyl radical or the like, the following acids are contemplated: benzoic, o-toluic, m-toluic, p-toluic, salicylic, anisic, phthalic, terephthalic, hemimellitic, trimellitic, trimesic, prehnitic, phenyacetic, hydrocinnamic, $\gamma$-phenylbutyric, $\delta$-phenyl-n-valeric, $\epsilon$-phenyl-n-caproic, homophthalic, o-phenylene diacetic, m-phenylene-diacetic, p-phenylene diacetic and o-phenyleneacetic-$\beta$-propionic acid.

Alkali and alkaline earth metal salts of these acids in mixtures with the acids may also be used. Thus the reaction can be carried out using sodium acetate, calcium acetate, potassium propionate, barium isobutyrate, calcium acetate, magnesium acetate, magnesium butyrate, sodium valerate, lithium trimethylacetate, barium caproate, calcium palmitate, sodium laurate, calcium caproate, and the like as part of the acid-producing ingredients.

Examples of $R'$ groups coming within the foregoing definition are methyl, ethyl, propyl, isopropyl, butyl, isobutyl, t-butyl, amyl, isoamyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, and eicosyl groups. Other acids that can be used include isovaleric, methylethylacetic, isocaproic, methyl-n-propylacetic, diethylacetic, sec-butylacetic, dimethylethylacetic, tert-butylacetic, methyl-isopropylacetic, methyl-t-butylneopentylacetic, myristic, palmitic, margaric, and dicetylacetic acid.

If a mixture of carboxylic acid and salt is used, such as $RCO_2H$ and $RCO_2Na$, the salt can be preformed by pretreating the acid feed to the reactor with sodium hydroxide, for example, or the salt can be added directly to the reactor.

The catalyst for the reaction comprises compounds of the noble metals of Group VIII of the Periodic Table, including compounds of palladium, iridium, osmium, ruthenium, rhodium, and platinum illustrative are the halides of these metals. Specific examples are platinum and palladium chlorides.

The reduction-oxidation system that is used to continuously maintain the catalyst in its oxidized form is brought about by compounds of metals which, under the reaction conditions, may be present in various oxidation stages. Examples are compounds of copper, mercury, lead, cerium, thallium, tin, titanium, vanadium, antimony, chromium, molybdenum, uranium, manganese, nickel, iron, cobalt, and osmium. Examples of suitable regenerative oxidants capable of maintaining the noble metal in oxidized form are cupric chloride, cupric bromide, cupric iodide, cupric acetate, cupric nitrate, cupric sulfate, mercuric acetate, mercuric bromate, mercuric bromide, mercuric iodide, mercuric carbonate, mercuric chloride, chromic bromide, chromic chloride, nickel chloride, nickel bromide, nickel iodide, ferric chloride, cobalt chloride, and osmium chloride. Other redox systems include iodide/iodine systems, arsenite/arsenate, sulfite/sulfate systems, or organic redox systems including oxobenzene/hydrazobenzene, or quinones or hydroquinones of the benzene, anthracene, or phenanthrene series.

The reaction may be carried out in a medium containing an active oxidizer, or in the presence of an active oxidizer such as oxygen, ozone, peroxidic compounds (especially hydrogen peroxide), oxides of nitrogen, free halogens, halogen-oxygen compounds, or compounds of the higher valence stages of metals such as manganese, cerium, chromium, selenium, lead, vanadium, silver, molybdenum, cobalt, and osmium. The presence of the active oxidizer promotes the reformation of the higher oxidation stage of the active catalyst component which is necessary for the promotion of the reaction. Some of these oxidizing agents may be produced during the reaction. In some instances it may be advantageous to add an oxidizing agent to the reaction as it proceeds. In general, any of the catalyst-oxidant systems used in the so-called Consortium process are suitable for use in the process of this invention. One of the most practical catalyst-oxidant systems is the combination of palladium chloride, anhydrous hydrogen chloride, and cupric chloride. Using this catalyst combination as an illustration, the various combinations of reactants and catalyst systems that are contemplated by this invention may be represented as follows:

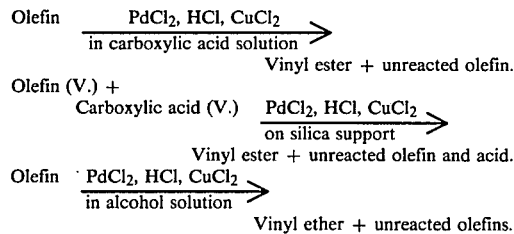

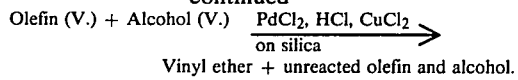

In all of the foregoing reactions, the feed stocks must be substantially anhydrous in order to avoid the formation of aldehydes and ketones, but this invention may also be used for the continuous and cyclic preparation of aldehydes and ketones by subjecting the vinyl ether or ester in the product stream to hydrolysis with water, preferably acidic water. The carbonyl compound is liberated along with the starting alcohol or acid. The unreacted oxygen, olefin, and liberated acid or alcohol are recycled to the reactor, and the carbonyl compound is scrubbed out, distilled, or extracted, depending on its nature.

For example, with ethylene and an alcohol, referring to the drawing, the feed mixture enters line 10 and reactor 12 wherein the catalyst, comprising a noble metal halide, haloacid, and heavy metal halide in alcohol solution, is maintained. The reaction produces a product mixture containing unreacted ethylene, vinyl ether, and unused oxygen, which is sent via line 14 to hydrolysis reactor 16. As the result of the hydrolysis, a water solution of acetaldehyde is drawn off at line 18 and an overhead comprising unused oxygen, ethylene, and alcohol (which is preferably water-insoluble) is taken off at line 20, sent to dryer 22, and recycled via line 24. The reaction can be carried out in an alcohol or acid carrier-reactant, and any make-up acid or alcohol is added at line 26.

This process has the advantage that the reactor can be maintained at any desired temperature, at atmospheric pressure, by proper selection of the alcohol or acid without distillation occurring. For example, when propionic acid is used, the temperature of the reactor can be maintained up to the boiling point of propionic acid. It is, of course, preferable that the acid or alcohol used be insoluble in water, and that the carbonyl compound liberated be soluble in water so that the aldehyde or ketone can be easily scrubbed out in the hydrolysis unit, but this is not a limitation. Other methods can be used to separate the carbonyl compound.

In order to illustrate the invention, the following examples are given:

EXAMPLE I

Ethylene in vapor form is passed through a reservoir of liquid acetic acid to vaporize a preselected amount of the acid, and the resulting mixture is passed through a bed of catalyst consisting of palladium chloride ($PdCl_2$), hydrogen chloride, and cupric chloride ($CuCl_2$) supported on silica. The vinyl acetate is removed as product from the effluent gas stream, and the unreacted ethylene is recycled to the reactor. The flow of ethylene and acetic acid to the reactor is interrupted periodically, and a stream of oxygen is passed through the catalyst bed to regenerate the oxidant.

EXAMPLE II

Ethylene in vapor form is passed through a reservoir of liquid acetic acid to vaporize a preselected amount of the acid, a small amount of air is added continuously to the resulting gas mixture, and the mixture is passed through a bed of catalyst consisting of palladium chloride, anhydrous hydrogen chloride, and cupric chloride supported on one-eighth-inch silica pellets. The vinyl acetate is removed as product from the effluent gas stream, and the unreacted ethylene and acetic acid are recycled to the reactor. The yield of vinyl acetate is found to remain substantially constant over several hundred hours of operation because the small amount of air in the feed stream maintains the regenerative oxidant of the catalyst system in oxidizing form.

EXAMPLE III

Ethylene in vapor form is passed through a reservoir of liquid ethanol to vaporize a preselected amount of the alcohol, and the resulting mixture is passed through a bed of catalyst consisting of palladium chloride (PdCl$_2$), hydrogen chloride, and cupric chloride (CuCl$_2$) supported on silica pellets. The vinyl ethyl ether is removed from the reactor effluent, and the unreacted ethylene and ethanol are recycled to the reaction zone.

EXAMPLE IV

Ethylene is passed through an anhydrous acetic acid solution of palladium chloride, hydrogen chloride, and cupric chloride. The resulting vinyl acetate is recovered from the reactor effluent stream, and the unreacted ethylene is recycled. After a few hours of operation, the introduction of ethylene is interrupted and a stream of dilute oxygen in nitrogen is passed through the acetic acid solution to regenerate the oxidant portion of the catalyst system.

EXAMPLE V

Ethylene containing a small amount of air is bubbled through an anhydrous acetic acid solution of sodium acetate, palladium chloride, hydrogen chloride, and cupric chloride. The resulting vinyl acetate is recovered from the reactor effluent stream and the unreacted ethylene, along with the nitrogen diluent, is recycled to the reaction solution while acetic acid containing sodium acetate is continuously added to the solution to replenish the amount consumed in the reaction. The small amount of oxygen in the air maintains the oxidant of the catalyst system in active form, permitting continuous operation of the reaction for a prolonged period of time.

In some cases, the reaction of the olefin and the alcohol tends to give mixtures of acetals and vinyl ether, or acetals alone. In these cases, the product gases are passed over catalysts which are known to eliminate alcohol from the acetal to give the vinyl ether. Thus:

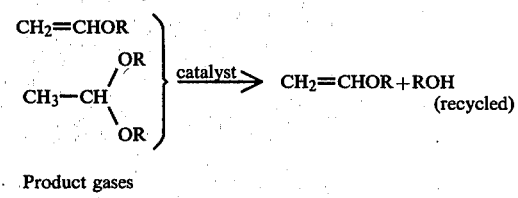

Product gases

Similar processes may be used with the product streams with acids which may contain alkylidene diacetates, for example, when acetic acid is used.

EXAMPLE VI

Ethylene is passed through an ethanolic solution of palladium chloride, hydrogen chloride, and cupric chloride. The resulting mixture of vinyl ethyl ether and diethyl acetal is removed from the reactor effluent stream, and the unreacted ethylene is recycled. The product mixture is then passed over a suitable catalyst, such as described in U.S. Pat. No. 1,931,858; Brit. Pat. No. 345,253; Ger. Pat. No. 525,836; and M. Cabanac, Compt. rend., 190, 881 (1930), and the vinyl ethyl ether is removed from the off gases. The liberated ethanol is recycled to the reactor.

The embodiments of the invention in which an exclusive property or privilege is claimed are defined as follows:

1. The process of preparing vinyl esters which comprises reacting an olefinic hydrocarbon having 2 to 10 carbon atoms per molecule with a carboxylic acid of the formula $$R^1(COOH)_m$$

wherein $R^1$ is a hydrocarbon radical of 1 to 20 carbon atoms and m is an integer of 1 to 5, under substantially anhydrous liquid phase conditions in the presence of a catalytic amount of a member selected from the group consisting of (a) an alkaline earth metal salt of a carboxylic acid within the above-defined group in combination with a noble metal compound selected from the group consisting of palladium, iridium, ruthenium, rhodium, and platinum; and (b) an alkali metal or alkaline earth metal salt of carboxylic acids within the above defined group in combination with a noble metal compound selected from platinum, iridium, ruthenium and rhodium compounds, and a regenerative oxidant capable of maintaining said noble metal in oxidized form.

2. The method of claim 1 wherein said olefin is reacted with said acid in the presence of (a) a member selected from platinum, iridium, ruthenium and rhodium compounds, (b) alkali and alkaline earth metal salts of acids within said defined group, and (c) said regenerative oxidant.

3. The method of claim 1 wherein said regenerative oxidant comprises compounds of members selected from the group consisting of copper, mercury, lead, cerium, thallium, tin, titanium, vanadium, antimony, chromium, molybdenum, uranium, manganese, nickel, iron, cobalt and osmium, which compounds may have various oxidation stages under the reaction conditions.

4. The method of claim 3 wherein said olefin is selected from the group consisting of hydrocarbon olefins having up to 10 carbon atoms per molecule, and said carboxylic acid is selected from monocarboxylic acids having 1 to 5 carbon atoms per molecule.

5. The method of claim 1 wherein said olefin is reacted with said acid in the presence of (a) a compound of palladium or platinum, (b) an alkaline earth metal salt of a hydrocarbon monocarboxylic acid within the above group, and (c) said regenerative oxidant is selected from the group consisting of compounds of copper, mercury, lead, cerium, thallium, tin, titanium, vanadium, antimony, chromium, molybdenum, uranium, manganese, nickel, iron, cobalt and osmium which may be present in various oxidation stages under reaction conditions.

6. The method of claim 5 wherein said noble metal compound is a palladium halide.

7. A process for producing the unsaturated ester of a carboxylic acid which comprises reacting, in the liquid phase, an olefinically unsaturated hydrocarbon having 2 to 10 carbon atoms with a carboxylic acid in the presence of an alkaline earth metal salt of a carboxylic acid, a palladous halide, a redox system and molecular oxygen under substantially anhydrous conditions.

8. A process for producing the unsaturated ester of a carboxylic acid which comprises reacting, in the liquid phase, an olefinically unsaturated hydrocarbon having 2 to 10 carbon atoms with a carboxylic acid in the presence of an alkali metal salt of a carboxylic acid, a member selected from platinum, iridium, ruthenium and rhodium halides, a redox system and molecular oxygen under substantially anhydrous conditions.